United States Patent [19]

Petersen

[11] E Re. 31,244

[45] Reissued May 17, 1983

[54] ANTIHYPERTENSIVE PYRIDYLGUANIDINE COMPOUNDS

[75] Inventor: Hans J. Petersen, Valby, Denmark

[73] Assignee: Leo Pharmaceutical Products Ltd. A/S (Lovens kemiske Fabrik Produktionsaktieselskab), Ballerup, Denmark

[21] Appl. No.: 314,023

[22] Filed: Oct. 22, 1981

Related U.S. Patent Documents

Reissue of:

[64] Patent No.: 4,057,636
Issued: Nov. 8, 1977
Appl. No.: 636,747
Filed: Dec. 1, 1975

[30] Foreign Application Priority Data

Dec. 20, 1974 [GB] United Kingdom ..... 55209/74

[51] Int. Cl.[3] ..... A61K 31/44; C07D 211/00

[52] U.S. Cl. ..... 424/263; 546/306

[58] Field of Search ..... 424/263; 546/306

[56] References Cited

U.S. PATENT DOCUMENTS 3,036,083 5/1962 Mull ..... 260/294.9 X
3,897,444 7/1975 Durant et al. ..... 260/294.9 X

*Primary Examiner*—Leonard Schenkman
*Attorney, Agent, or Firm*—Cushman, Darby & Cushman

[57] ABSTRACT

The invention relates to a series of new compounds, to methods for preparing the compounds, to compositions containing said compounds which are useful in the human and veterinary medical practice, and to methods for treating patients suffering from certain illnesses with said compounds, the new compounds having the general formula I

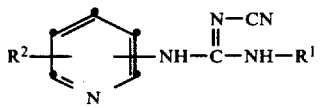

I or the tautomeric forms thereof in which the $R^1$-substituted cyano-guanidyl radical is placed in the 2-, 3- or 4-position of the pyridine ring, and in which $R^1$ stands for a straight or branched, saturated or unsaturated, aliphatic hydrocarbon radical having from 1 to 8 carbon atoms, a cycloalkyl or cycloalkenyl radical having from 3 to 7 carbon atoms, an aryl or an aralkyl radical, and $R^2$ stands for hydrogen, halogen, hydroxy, lower alkyl or alkoxy radicals; and in the case of the present compounds containing one or more asymmetric carbon atoms, also the stereoisomers thereof and racemic mixtures of same; and salts of the compounds of formula I with nontoxic, pharmaceutically acceptable acids.

The new compounds of the invention have surprisingly shown to be highly potent hypotensive compounds giving rise to a pronounced reduction of the blood pressure. They have a low toxicity and consequently a high therapeutic ratio.

22 Claims, No Drawings

ANTIHYPERTENSIVE PYRIDYLGUANIDINE COMPOUNDS

Matter enclosed in heavy brackets [ ] appears in the original patent but forms no part of this reissue specification; matter printed in italics indicates the additions made by reissue.

The present invention relates to a series of new compounds, to methods for preparing the compounds, to compositions containing said compounds which are useful in the human and veterinary medical practice, and to methods for treating patients suffering from certain illnesses with said compounds.

The new compounds have the general formula I

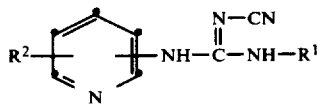

I or the tautomeric forms thereof in which the $R^1$-substituted cyano-guanidyl radical is placed in the 2-, 3- or 4-position of the pyridine ring, and in which $R^1$ stands for a straight or branched, saturated or unsaturated, aliphatic hydrocarbon radical having from 1 to 8 carbon atoms, a cycloalkyl or cycloalkenyl radical having from 3 to 7 carbon atoms, an aryl or an aralkyl radical, and $R^2$ stands for hydrogen, halogen, hydroxy, lower alkyl or alkoxy radicals. More particularly, $R^1$ may represent a methyl, ethyl, propyl, isopropyl, butyl, isobutyl, sec-butyl, or tert-butyl radical, or one of the isomeric pentyl radicals, e.g. tert-pentyl and neopentyl, isomeric hexyl radicals e.g. 1-methyl-1-ethylpropyl, or isomeric heptyl radicals e.g. the 1,1-diethylpropyl radical or corresponding alkenyl radicals, a cyclopropyl, cyclobutyl, cyclopentyl, dimethylcyclobutyl, methylcyclopentyl, a cyclohexyl or a cycloheptyl radical, a cyclopentenyl, cyclohexenyl or cycloheptenyl radical, a phenyl or substituted phenyl radical, a benzyl, or a phenylethyl radical.

In the case where the present compounds contain one or more asymmetric carbon atoms, these compounds may form stereoisomers. The present invention also comprises such stereoisomers and racemic mixtures of same.

The present invention further comprises nontoxic, pharmaceutically acceptable salts of the compounds of formula I with acids.

The new compounds of the invention have surprisingly shown to be highly potent hypotensive compounds giving rise to a pronounced reduction of the blood pressure. They have a low toxicity and consequently a high therapeutic ratio.

The effect is unexpected, as the literature, (J. Med. Chem. Vol. 11, p. 811 (1968)) which describes cyanoguanidines of the formula

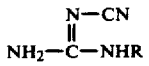

as having hypotensive effect although of a much lower potency than the compounds of the present invention, further states that when the free amino group is substituted the hypotensive effect is totally lost.

In the light of this statement it has been a most remarkable finding that the compounds of the present invention have a potency which is by far exceeding that of e.g. "Guancydine", which is the most potent of the compounds of the above-mentioned literature and which is N-cyano-N'-tert-pentylguanidine.

The new compounds of the invention have been shown to exert a strong and prolonged antihypertensive effect in various animal species when administered enterally or parenterally. In the range of antihypertensive doses as well as with higher doses the compounds are devoid of any effect on the central nervous system. The only collateral effect observed is a compensatory tachycardia. It is believed that these compounds exert their antihypertensive action through a peripheral effect on blood vessels.

Thus, it has surprisingly been found that the present compounds have a favourable therapeutic index, by enteral as well as parenteral administration, relieving hypertensive conditions and being well-tolerated compounds which in preliminary experiments have not shown any adverse effects.

The invention also comprises methods for the preparation of the above described compounds.

In one method of 2-, 3- or 4-pyridyl carbodiimide of the formula II

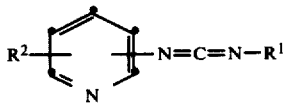

II in which $R^1$ and $R^2$ are as defined above is reacted with cyanamide. The reaction can be performed at or about room temperature and with or without use of ordinary solvents. The reaction may in some cases preferably be accelerated by addition of basic catalysts, such as e.g. a tert.amine.

In another embodiment of the method a compound of the formula III

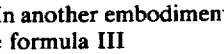

III in which R' stands for $R^1$ as defined above or for a $R^2$-substituted 2-, 3- or 4-pyridyl radical, is reacted with an amine $NH_2R''$, in which R'' is a $R^2$-substituted 2-, 3- or 4-pyridyl radical when R' is $R^1$, and in which R'' is $R^1$ when R' is a $R^2$-substituted 2-, 3- or 4-pyridyl radical.

The reaction can be carried through, if necessary in a suitable solvent, at a temperature from about 0° C. to a temperature about the boiling point of the solvent used. The reactants can be used in equivalent amounts, but it may be preferable to use an excess of the amine in question.

As examples of suitable solvents, mention may be made of diethyl ether, chloroform, acetone, pyridine, acetonitrile, and ethanol. In some instances it will be possible to use certain of the amines $R''—NH_2$ as reaction medium.

In still another embodiment a compound of the formula IV

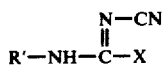

IV in which R′ is as defined above and X is halogen, preferably chlorine, a lower alkylthio radical or a lower alkoxy radical, is reacted with an amine $NH_2$—R″, in which R″ is as defined above. This reaction can preferably be carried out in the presence of an inert organic solvent, and in the case when X stands for a halogen atom it may be preferable to use an excess of amine or another acid binding agent, such as a tertiary amine.

In still another embodiment a compound of the formula V

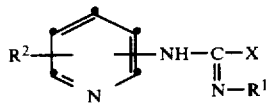

V in which $R^1$, $R^2$ and X are as defined above is reacted with cyanamide under conditions similar to those described above. The starting materials in the above processes are known compounds or analogues which can be prepared in similar manner as the known ones.

In still another embodiment a thiourea of the formula VI

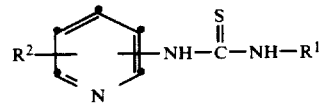

VI in which $R^1$ and $R^2$ have the above meanings, is converted to the corresponding compound of formula I by treatment with a salt of cyanamide, preferably a metal salt, e.g. the lead salt.

The compounds of formula II may be prepared from the corresponding ureas or thioureas by conventional methods, e.g. by treating with triphenylphosphine, carbon tetrachloride and triethylamine in dry methylene chloride or by treatment with phosgene in an inert solvent, e.g. tetrahydrofuran, preferably at low temperature. By addition of a tertiary amine to the imidochloride formed the desired compound can be obtained.

The starting materials of formula III can in analogous manner be obtained from the corresponding N-cyano-substituted ureas or thioureas.

The starting materials of formula IV in which X stands for lower alkoxy or alkylthio may be obtained by reacting cyanamide with a pyridylisocyanate or a pyridylisothiocyanate in the presence of a tertiary amine followed by treatment with a lower alkyl iodide.

Some of the starting materials of formula IV where X stands for lower alkylthio can alternatively be prepared by reacting a S-di-lower alkyl cyanodithioimidocarbonate with the appropriate amine. This alternative is also well known from the literature.

When in the compounds of formula IV X stands for chlorine these imidochlorides are obtained from the N-cyano substituted ureas or thioureas as described above.

When in the compounds of formula V X stands for chlorine such imidochlorides can be obtained from the corresponding ureas or thioureas as described above.

In the methods above, a desired stereoisomer may be obtained by using the corresponding isomer of the starting material in the preparation.

Alternatively, the racemate may be used as starting material, whereafter the resulting mixture may be subjected to a racemate resolution, e.g. by crystallization of a suitable salt with an optically active, strong acid, in known manner.

It is a further object of the present invention to provide pharmaceutical compositions which are useful in the treatment of hypertension.

With this object in view, the compositions of the invention contain as an active component at least one member selected from the group consisting of compounds of the formula I and salts thereof with nontoxic, pharmaceutically acceptable acids, together with solid or liquid pharmaceutical carriers and/or auxiliary agents.

Said compositions should contain at least 0.1% of the therapeutically active compound and can be worked up to various pharmaceutical forms of presentation, such as tablets, pills, dragees, capsules, sustained release tablets, suspensions, suppositories, injection medicine, containing the compounds of formula I or their atoxic salts, mixed with carriers and/or auxiliary agents.

Pharmaceutical organic or inorganic, solid or liquid carriers and/or auxiliary agents suitable for oral, or enteral administration can be used to make up compositions containing the present compounds. Gelatine, lactose, starch, magnesium stearate, talc, vegetable and animal fats and oils, gum, polyalkylene glycol, buffers or other known carriers and/or auxiliary agents for medicaments are all suitable.

The compositions may further contain other therapeutic compounds applied in the treatment of hypertension, besides the well known auxiliary agents. Such other compounds may be, for instance β-adrenergic blockers, diuretics, reserpine, and α-methyldopa. The combination with a β-adrenergic blocker seems particularly advantageous, because the compensatory tachycardia observed as a collateral effect in connection with the use of the present compounds may be avoided.

Another object of the invention resides in the selection of a dose of the compounds of the invention, which dose can be administered so that the desired activity is achieved without simultaneous secondary effects.

In the human therapy, the compounds and their salts can conveniently be administered (to adults) in dosage units containing not less than 0.01 mg and up to 1000 mg, preferably from 0.02 to 200 mg, calculated as the compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

In the form of dosage units, the compounds may be administered once or more times a day at appropriate invervals, always depending, however, on the condition of the patient, and in accordance with the prescription made by the medical practitioner.

In the continuous therapy of patients suffering from hypertension, tablets or capsules may be the appropriate form of pharmaceutical preparation owing to the prolonged effect obtained when the drug is given orally, in particular in the form of sustained-release tablets.

In the treatment of hypertension, such tablets may advantageously contain other active components, as mentioned hereinbefore.

Some of the ureas and thioureas used as starting materials are known from the literature, and the hitherto unknown can be prepared by methods analogous to those described. In the following table a number of ureas and thioureas used are characterized by their melting points. They are e.g. prepared by reacting 1-1.5 equivalent of the amine in question with about 1 equivalent of the pyridylisocyanate or -isothiocyanate or of the S-methyl pyridyldithiocarbamate in a suitable inert solvent, e.g. diethyl ether, ethanol, chloroform, acetone, pyridine, acetonitrile, and at a temperature from about 0° C. to about the boiling point of the solvent used, preferably at room temperature.

TABLE A

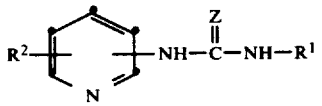

| $R^1$ | 2-, 3- or 4-pyridyl | $R^2$ | Melting point °C. |
|---|---|---|---|
| Z = S | | | |
| isopropyl | 2 | H | 129.0-130.0 |
| tert-butyl | 2 | H | 157.0-158.0 |
| cyclopentyl | 2 | H | 149.5-150.5 |
| tert-butyl | 3 | H | 143.5-144.0 |
| 1-ethyl-1-methyl-propyl | 3 | H | 122.0-123.0 |
| 1,1-dimethylbutyl | 3 | H | 104.0-104.5 |
| 1,1-diethylpropyl | 3 | H | 149.5-150.5 |
| tert-pentyl | 3 | H | 134.5-135.5 |
| neopentyl | 3 | H | 139.0-139.5 |
| isopropyl | 3 | H | 123.0-124.0 |
| 1-ethylpropyl | 3 | H | 90.0-90.5 |
| n-butyl | 3 | H | 102.0-103.0 |
| n-pentyl | 3 | H | 102.0-103.0 |
| n-hexyl | 3 | H | 98.0-99.0 |
| cyclopentyl | 3 | H | 135.5-136.5 |
| 1-methylcyclopentyl | 3 | H | 146.0-146.5 |
| cyclohexyl | 3 | H | 148.0-149.0 |
| cyclooctyl | 3 | H | 123.0-124.0 |
| cyclopropyl | 3 | H | 155.0-155.5 |
| cyclobutyl | 3 | H | 143.5-144.0 |
| 1-methylcyclobutyl | 3 | H | 150.0-151.0 |
| isobutyl | 3 | H | 121.0-122.0 |
| sec-butyl | 3 | H | 117.0-118.0 |
| 2-methylbutyl | 3 | H | 86.0-87.0 |
| 1,2,2-trimethylpropyl | 3 | H | 130.0-130.5 |
| 1,1,2-trimethylpropyl | 3 | H | 109.5-110.0 |
| 1,3-dimethylbutyl | 3 | H | 108.0-109.0 |
| 1,1,3-trimethylbutyl | 3 | H | 96.5-97.0 |
| 1,1,3,3-tetramethyl-butyl | 3 | H | 106.0-107.0+ |
| allyl | 3 | H | 96.0-96.5 |
| +hydrate | | | |
| 2-methylallyl | 3 | H | 102.0-102.5 |
| phenyl | 3 | H | 159.0-160.0 |
| 4-methoxyphenyl | 3 | H | 115.0-116.0 |
| 2,6-dichlorophenyl | 3 | H | 148.0-149.0 |
| benzyl | 3 | H | 136.0-136.5 |
| α-methylbenzyl | 3 | H | 157.0-158.0 |
| α,α-dimethylbenzyl | 3 | H | 153.5-154.0 |
| β-phenylethyl | 3 | H | 121.5-122.0 |
| tert-butyl | 3 | 5-Br | 126.0-127.0 |
| cyclopentyl | 3 | 6-$OCH_3$ | 139.0-140.0 |
| tert-butyl | 3 | (3-quinolyl) | 163.5-164.5 |
| tert-butyl | 4 | H | 138.5-139.5 |
| n-pentyl | 4 | H | 93.0-93.5 |
| tert-phenyl | 4 | H | 129.5-130.5 |
| neopentyl | 4 | H | 118.5-119.5 |
| cyclopentyl | 4 | H | 131.0-132.0 |
| 1-methylcyclopentyl | 4 | H | 157.5-158.5 |
| 1,1-diethylpropyl | 4 | H | 129.5-130.0 |
| 1,1,2-trimethylpropyl | 4 | H | 172.0-172.5+ |
| 1,1,3-trimethylbutyl | 4 | H | 130.5-131.5 |
| benzyl | 4 | H | 148.0-150.0 |
| +hydrochloride | | | |
| Z = O | | | |
| n-butyl | 3 | H | 88.0-89.0 |
| tert-butyl | 3 | H | 146.0-146.5 |
| neopentyl | 3 | H | 107.0-108.0 |

TABLE A-continued

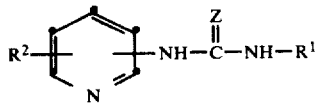

| $R^1$ | 2-, 3- or 4-pyridyl | $R^2$ | Melting point °C. |
|---|---|---|---|
| tert-pentyl | 3 | H | 64.0-64.5++ |
| 1-ethylpropyl | 3 | H | 104.0-105.0 |
| 1,3-dimethylbutyl | 3 | H | 56.0-59.0++ |
| 1,2,2-trimethylpropyl | 3 | H | 70.0-71.0++ |
| 1,1-dimethylbutyl | 3 | H | 88.0-88.5 |
| 1,1,3-trimethylbutyl | 3 | H | 72.0-72.5++ |
| 1,1-diethylpropyl | 3 | H | 95.5-96.0 |
| 2-ethylhexyl | 3 | H | 172.0-172.5+ |
| 1,1,3,3,tetramethyl-butyl | 3 | H | 110.0-111.0++ |
| cyclohexyl | 3 | H | 93.0-95.0++ |
| cyclooctyl | 3 | H | 57.0-58.0++ |
| phenyl | 3 | H | 169.0-169.5 |
| α-methylbenzyl | 3 | H | 102.5-103.5 |
| tert-butyl | 3 | 5-Br | 176.5-177.0 |

+hydrochloride
++hydrate

Whenever the expression "lower" is used in the foregoing and in the following in connection with an organic radical it indicates a content of from 1 to 6 carbon atoms.

The invention will now be further described in the following non-limiting Examples

EXAMPLE 1

N-tert-Butyl-N''-cyano-N'-3-pyridylcuanidine

N-tert-butyl-N'-3-pyridylcarbodimide (5.25 g) was mixed with cyanamide (1.36 g), while stirring at room temperature. A catalytic amount of N,N-diisopropylethylamine was added, and the mixture was left at ambient temperature for 20 hours, while complete solidification gradually occurred. The solid mass was powdered and consecutively stirred with petroleum ether and water to yield the crude product. Recrystallisation was performed by dissolving in a slight excess of 0.5 N hydrochloric acid, treating with charcoal, filtering through celite and precipitating by addition of excess saturated aqueous sodium carbonate. Mp: 205.0°-206.5° C., IR(KBr): Strong absorption at 2170 $cm^{-1}$ (—C≡N).

The carbodimide used as starting material was prepared as follows:

N-tert-Butyl-N'-3-pyridylthiourea (12.6 g) was suspended in dry tetrahydrofuran (125 ml) at 0° C. While stirring vigorously, a 1.2 M solution of phosgene in toluene (69 ml) was introduced. The mixture was kept at 0° C. for 5 hours, then evaporated in vacuo. After adding a small amount of tetrahydrofuran the evaporation was repeated.

The residue was suspended in tetrahydrofuran (100 ml) at 0° C., and N,N-diisopropylethylamine (20.4 ml) was added. The slurry was evaporated in vacuo and the residue was extracted with petroleum ether (200 ml), charcoaled and filtered. On evaporation in vacuo the filtrate yielded the desired carbodiimide in quantitative yield; IR($CHCl_3$) showed a characteristic strong absorption band at 2120-2140 $cm^{-1}$ (—N=C=N—).

EXAMPLE 2

N''-cyano-N-(1-ethyl-1-methylpropyl)-N'-3-pyridylguanidine

By following the procedure of Example 1, but substituting N-(1-ethyl-1- methylpropyl)-N'-3-pyridylcarbodiimide for the N-tert-butyl-N'-3-pyridylcarbodiimide, the N''-cyano-N-(1-ethyl-1-methylpropyl)-N'-3-pyridylguanidine was obtained with a melting point of 184.5°-186.0° C.

EXAMPLE 3

N''-cyano-N-(1,1-dimethylbutyl)-N'-3-pyridylcuanidine

By following the procedure of Example 1, but substituting N-(1,1-dimethylbutyl)-N'-3-pyridylcarbodiimide for the N-tert-butyl-N'-3-pyridylcarbodiimide, the N''-cyano-N-(1,1-dimethylbutyl)-N'-3-pyridylguanidine was obtained with a melting point of 188.0°-188.5° C.

EXAMPLE 4

N''-cyano-N-(1,1-diethylpropyl)-N'-3-pyridylguanidine

By following the procedure in Example 1, but substituting N-(1,1-diethylpropyl)-N'-3-pyridylcarbodiimide for the N-tert-butyl-N'-3-pyridylcarbodiimide, the N''-cyano-N-(1,1-diethylpropyl)-N'-3-pyridylguanidine was obtained with a melting point of 192.5°-193.5° C.

EXAMPLE 5

N''-cyano-N-tert-pentyl-N'-3-pyridylguanidine

By following the procedure of Example 1, but substituting N-tert-pentyl-N'-3-pyridylcarbodiimide for the N-tert-butyl-N'-3-pyridylcarbodiimide, the N''-cyano-N-tert-pentyl-N'-3-pyridylguanidine was obtained with a melting point of 187.0°-187.5° C.

EXAMPLE 6

N''-cyano-N-neopentyl-N'-3-pyridylguanidine

By following the procedure of Example 1, but substituting N-neopentyl-N'-3-pyridylcarbodiimide for the N-tert-butyl-N'-3-pyridylcarbodiimide, the N''-cyano-N-neopentyl-N'-3-pyridylguanidine was obtained with a melting point of 214.0°-215.0° C.

EXAMPLE 7

N''-cyano-N-isopropyl-N'-3-pyridylguanidine

By following the procedure of Example 1, but substituting N-isopropyl-N'-3-pyridylcarbodiimide for the N-tert-butyl-N'-3-pyridylcarbodiimide, the N''-cyano-N-isopropyl-N'-3-pyridylguanidine was obtained with a melting point of 154.5°-155.0° C. Warning: Strongly exothermic reaction was observed in this case.

EXAMPLE 8

N''-cyano-N-1-ethylpropyl-N'-3-pyridylguanidine

By following the procedure of Example 1, but substituting N-1-ethylpropyl-N'-3-pyridylcarbodiimide for the N-tert-butyl-N'-3-pyridylcarbodiimide, the N''-cyano-N-1-ethylpropyl-N'-3-pyridylguanidine was obtained with a melting point of 109.5°-110.5° C.

EXAMPLE 9

N-n-Butyl-N''-cyano-N'-3-pyridylguanidine

By following the procedure of Example 1, but substituting N-n-Butyl-N'-3-pyridylcarbodiimide for the N-tert-butyl-N'-3-pyridylcarbodiimide, the desired compound was obtained with a melting point of 96.0°-97.0° C.

Warning: Exothermic reaction!

EXAMPLE 10

N-sec.-butyl-N''-cyano-N'-3-pyridylguanidine

By following the procedure of Example 1, but substituting N-sec-butyl-N'-3-pyridylcarbodiimide for the N-tert-butyl-N'-3-pyridylcarbodiimide, the desired compound was obtained with a melting point of 133.5°-135.0° C.

EXAMPLE 11

N''-cyano-N-n-pentyl-N'-3-pyridylguanidine

By following the procedure of Example 1, but substituting N-n-pentyl-N'-3-pyridylcarbodiimide for the N-tert-butyl-N'-3-pyridylcarbodiimide, the desired compound was obtained with a melting point of 130.4°-131.6° C.

EXAMPLE 12

N''-cyano-N-1-methylcyclobutyl-N'-3-pyridylguanidine

By following the procedure of Example 1, but substituting N-1-methylcyclobutyl-N'-3-pyridylcarbodiimide for the N-tert-butyl-N'-3-pyridylcarbodiimide, the desired compound was obtained with a melting point of 210.5°-211.5° C.

EXAMPLE 13

N''-cyano-N-3-pyridyl-N'-1,1,2-trimethylpropylguanidine

By following the procedure of Example 1, but substituting N-3-pyridyl-N'-1,1,2-trimethylpropylcarbodiimide for the N-tert-butyl-N'-3-pyridylcarbodiimide, the desired compound was obtained with a melting point of 194.0°-195.0° C.

EXAMPLE 14

N''-cyano-N-3-pyridyl-N'-1,2,2-trimethylpropylguanidine

By following the procedure of Example 1, but substituting N-3-pyridyl-N'-1,2,2-trimethylpropylcarbodiimide for the N-tert-butyl-N'-3-pyridylcarbodiimide, the desired compound was obtained with a melting point of 167.5°-168.5° C.

EXAMPLE 15

N''-cyano-N-3-pyridyl-N'-1,1,3-trimethylbutylguanidine

By following the procedure of Example 1, but substituting N-3-pyridyl-N'-1,1,3-trimethylbutylcarbodiimide for the N-tert-butyl-N'-3-pyridylcarbodiimide, the desired compound was obtained with a melting point of 180.5°-181.5° C.

EXAMPLE 16

N''-cyano-N-3-pyridyl-N'-1,1,3,3-tetramethylbutylguanidine

By following the procedure of Example 1, but substituting N-3-pyridyl-N'-1,1,3,3,-tetramethylbutylcarbodiimide for the N-tert-butyl-N'-3-pyridylcarbodiimide, the desired compound was obtained with a melting point of 180.5°-181.5° C.

EXAMPLE 17

N-3-(5-bromopyridyl)-N'-tert-butyl-N''-cyanoguanidine

By following the procedure of Example 1, but substituting N-3-(5-bromopyridyl)-N''-tert-butylcarbodiimide for the N-tert-butyl-N'-3-pyridylcarbodiimide, the desired compound was obtained with a melting point of 153.0°-153.5° C.

EXAMPLE 18

N-tert-butyl-N''-cyano-N'-5-(2-methoxypyridyl)guanidine

By following the procedure of Example 1, but substituting N-tert-butyl-N'-5-(2-methoxypyridyl)carbodiimide for the N-tert-butyl-N'-3-pyridylcarbodiimide, the desired compound was obtained with a melting point of 156.0°-157.0° C.

EXAMPLE 19

N-tert-butyl-N'-3-(2-chloropyridyl)-N''-cyanoguanidine

By following the procedure of Example 1, but substituting N-tert-butyl-N'-3-(2-chloropyridyl)carbodiimide for the N-tert-butyl-N'-3-pyridylcarbodiimide, the desired compound was obtained with a melting point of 202.0°-203.0° C.

EXAMPLE 20

N-tert-butyl-N''-cyano-N'-pyridylguanidine

By following the procedure of Example 1, but substituting N-tert-butyl-N'-2-pyridylcarbodiimide for N-tert-butyl-N'-3-pyridylcarbodiimide, the desired compound was obtained. the IR spectrum (KBr) showed a characteristic strong absorption band at 2160-70 $cm^{-1}$ (—C≡N). Melting point 168.0°-168.5° C. (dec.).

EXAMPLE 21

N''-cyano-N-cyclobutyl-N'-3-pyridylguanidine

By following the procedure of Example 1, but substituting N-cyclobutyl-N'-3-pyridylcarbodiimide for N-tert-butyl-N'-3-pyridylcarbodiimide, the desired compound was obtained. The IR spectrum (KBr) showed a strong absorption band at 2160-70 $cm^{-1}$.

EXAMPLE 22

N''-cyano-N-1,3-dimethylbutyl-N'-3-pyridylguanidine

By following the procedure of Example 1, but substituting N-1,3-dimethylbutyl-N'-3-pyridylcarbodiimide for N-tert-butyl-N'-3-pyridylcarbodiimide, the desired compound was obtained. IR(KBr) had a strong absorption band at 2160-70 $cm^{-1}$.

EXAMPLE 23

N''-cyano-N-phenyl-N'-3-pyridylguanidine

By following the procedure of Example 1, but substituting N-phenyl-N'-3-pyridylcarbodiimide for N-tert-butyl-N'-3-pyridylcarbodiimide, the desired compound was obtained.

EXAMPLE 24

N''-cyano-N-cyclopentyl-N'-5-(2-methoxypyridyl)-guanidine

By following the procedure of Example 1, but substituting N-cyclopentyl-N'-5-(2-methoxypyridyl)carbodiimide for N-tert-butyl-N'-3-pyridylcarbodiimide, the desired compound was obtained. IR(KBr) showed a strong absorption band at 2160-70 $cm^{-1}$.

EXAMPLE 25

N''-Cyano-N-cyclopentyl-N'-2- pyridylguanidine

By following the procedure of Example 1, but substituting N-cyclopentyl-N'-2-pyridylcarbodiimide for N-tert-butyl-N'-3-pyridylcarbodiimide, the desired compound was obtained.

EXAMPLE 26

N-n-Butyl-N''-cyano-N'-3-pyridylguanidine

To cyanamide (0.95 g) in ethanol (10 ml) was added N,N-diisopropylethylamine (3.4 ml), followed by 3-pyridylisothiocyanate (2.25 g), while stirring at 0° C. The mixture was left overnight at 0° C., then exhaustively evaporated in vacuo. The residue was stirred with ether (100 ml) to bring about crystallization of the N,N-diisopropylethylamine salt of N-cyano-N'-3-pyridylthiourea, which was filtered off and washed with ether. [The free thiourea could be isolated by suspending the salt in water and acidifying to pH 3-4 with hydrochloric acid. Melting point 184.5°-185.0° C. IR(KBr): Absorption at 2145 $cm^{-1}$ (—C≡N)] The amine salt (6.25 g) was suspended in dry DMF (15 ml), while stirring at 0° C. Methyl iodide (1.65 ml) was added dropwise and the gradually clearing solution was stirred for 1 hour, then left overnight at 0° C. After allowing the solution to heat to room temperature, it was evaporated in vacuo, finally under high vacuum at 25° C. Addition of ice-water (15 ml) and saturated aqueous $NaHCO_3$ (2.5 ml) brought about crystallization of S-methyl-N'-cyano-N-3-pyridylisothiourea as a hydrate, which was collected by filtration and washed with water. Melting point 153.5°-155.0° C. IR(KBr): Absorption at 2160-2180 $cm^{-1}$ (—C≡N)

The isothiourea (2.28 g) was dissolved in pyridine (25 ml), n-butylamine (10 ml) was added, and the mixture was left at room temperature for 72 hours, when it was evaporated in vacuo. The residue was stirred with water (30 ml) to effectuate crystallization. The product was filtered off and washed with water to yield the crude product. The compound was further purified by recrystallization from acetone-petroleum ether. Melting point 96.0°-97.0° C. The IR-spectrum (KBr) showed a strong —C≡N absorption band at 2165 $cm^{-1}$ and a broad absorption at 1600-1550 $cm^{-1}$. The spectrum was completely identical with that of the n-butyl substituted compound, prepared in example 9.

EXAMPLE 27

N''-Cyano-N-n-propyl-N'-3-pyridylguanidine

By following the procedure of Example 26, but substituting n-propylamine for n-butylamine, the desired compound was obtained with a melting point of 164.0°-165.0° C.

EXAMPLE 28

N''-Cyano-N-cyclopropyl-N'-3-pyridylguanidine

By following the procedure of Example 26, but substituting cyclopropylamine for n-butylamine, the desired compound was obtained with a melting point of 171.0°-172.0° C.

EXAMPLE 29

N''-Cyano-N-isobutyl-N'-3-pyridylguanidine

By following the procedure of Example 26, but substituting isobutylamine for n-butylamine, the desired compound was obtained with a melting point of 148.0°-149.0° C.

EXAMPLE 30

N''-Cyano-N-neopentyl-N'-3-pyridylguanidine

By following the procedure of Example 26, but substituting neopentylamine for n-butylamine, the desired compound was obtained with a melting point of 214.0°-215.0° C.+)

+)identical with the compound prepared in Example 6.

EXAMPLE 31

N''-Cyano-N-isopentyl-N'-3-pyridylguanidine

By following the procedure of Example 26, but substituting isopentylamine for n-butylamine, the desired compound was obtained with a melting point of 135.5°-136.5° C.

EXAMPLE 32

N''-Cyano-N-cyclopentyl-N'-3-pyridylguanidine

By following the procedure of Example 26, but substituting cyclopentylamine for n-butylamine, the desired compound was obtained with a melting point of 155.0°-156.0° C.

EXAMPLE 33

N''-Cyano-N-cyclohexyl-N'-3-pyridylguanidine

By following the procedure of Example 26, but substituting cyclohexylamine for n-butylamine, the desired compound was obtained with a melting point of 185.0°-186.0° C.

EXAMPLE 34

N''-Cyano-N-n-heptyl-N'-3-pyridylguanidine

By following the procedure of Example 26, but substituting n-heptylamine for n-butylamine, the desired compound was obtained with a melting point of 90.0°-91.0° C.

EXAMPLE 35

N''-Cyano-N-2-ethylhexyl-N'-3-pyridylguanidine

By following the procedure of Example 26, but substituting 2-ethylhexylamine for n-butylamine, the desired compound was obtained with a melting point of 84.0°-85.0° C.

EXAMPLE 36

N''-Cyano-N-2-methylallyl-N'-3-pyridylguanidine

By following the procedure of Example 26, but substituting 2-methylallylamine for n-butylamine, the desired compound was obtained with a melting point of 140.0°-141.0° C.

EXAMPLE 37

N-Benzyl-N''-cyano-N'-3-pyridylguanidine

By following the procedure of Example 26, but substituting benzylamine for n-butylamine, the desired compound was obtained with a melting point of 189.0°-190.0° C.

EXAMPLE 38

N''-Cyano-N-2-methylbutyl-N'-3-pyridylguanidine

By following the procedure of Example 26, but substituting 2-methylbutylamine for n-butylamine, the desired compound was obtained. IR (KBr) had a characteristic strong absorption band at 2160-70 $cm^{-1}$.

EXAMPLE 39

N''-Cyano-N-β-phenylethyl-N'-3-pyridylguanidine

By following the procedure of Example 26, but substituting β-phenylethylamine for n-butylamine the desired compound was obtained.

EXAMPLE 40

Hypotensive activity in normotensive anesthetized rats of the compound of Example 1, in the following called P 1060.

Male albino Sprague Dowley strain rats were anaesthetized with pentobarbital and fastened to rat boards in a supine position. The left carotid artery was exposed and cannulated with polyethylene cannula connected through a Statham pressure transducer to a Grass Polygraph Recorder. The right femoral vein was also canullated for the administration of P 1060. The compound was dissolved in dilute HCl. The volume administered did not exceed 0.2 ml. Table 1 summarizes the effects on mean blood pressure at the time of peak effect.

TABLE 1

| Treatment | Dose i.v. mg/kg | duration minutes | Δ mean blood pressure mm Hg |
|---|---|---|---|
| P 1060 | 0.002 | 3 | −70 |
| P 1060 | 0.005 | 12 | −70 |
| P 1060 | 0.010 | >45 | −85 |

EXAMPLE 41

Antihypertensive activity in conscious spontaneously hypertensive rats of the compounds of Examples 1, 2, 3, 4 and 5 in the following called P 1060, P 1066, P 1067, P 1068 and P 1075 respectively Male albino rats, spontaneously hypertensive Okamoto strain, fasting 16 hours before the experiments were used. The conscious animals were restrained in a plastic cage and a cuff was secured around the tail. The cuff was connected with an electronic blood pressure recorder. The systolic blood pressure and the heart rate were measured before and 2, 4, 6, and 24 hours after the administration of compounds. The compounds were suspended or dissolved in carboxymethylcellulose 0.5%. The volume administered did not exceed 0.5 ml/rat. Table 2 summarizes the results. There are also included, for comparison, the results obtained under the same experimental conditions with some known antihypertensive drugs, and the approximate oral $LD_{50}$ in mice are stated.

TABLE 2

| Dose | Before | | 2 hours | | 4 hours | | 6 hours | | 24 hours | |
|---|---|---|---|---|---|---|---|---|---|---|
| mg/kg | BP | HR | BP | HR | BP | HR | BP | HR | BP | HR |
| P 1060 | | | | | $LD_{50}$ > 1000 mg/kg p.o. (mice) | | | | | |
| 1.0 | 166 | 337 | <100 | — | <100 | — | <100 | — | 126 | 405 |
| 0.5 | 167 | 378 | <100 | — | <100 | — | <100 | — | 153 | 413 |
| 0.1 | 160 | 366 | 118 | 420 | <100 | 426 | 114 | 422 | 170 | 408 |
| 0.05 | 163 | 401 | 126 | 422 | 132 | 420 | 127 | 410 | 170 | 386 |
| 0.01 | 167 | 378 | 141 | 419 | 145 | 423 | 146 | 428 | 176 | 402 |
| P 1066 | | | | | $LD_{50}$ > 1000 mg/kg p.o. (mice) | | | | | |
| 10.0 | 177 | 369 | <100 | — | <100 | — | <100 | — | 126 | 336 |
| 2.5 | 171 | 375 | 113 | 386 | 100 | — | 114 | 375 | 152 | 335 |
| 0.5 | 173 | 384 | 146 | 437 | 143 | 413 | | | 181 | 413 |
| 0.05 | 172 | 408 | 155 | 462 | 170 | 417 | | | 178 | 413 |
| P 1067 | | | | | $LD_{50}$ > 1000 mg/kg p.o. (mice) | | | | | |
| 0.5 | 172 | 408 | 158 | 440 | 168 | 413 | | | 176 | 408 |
| P 1068 | | | | | $LD_{50}$ > 1000 mg/kg p.o. (mice) | | | | | |
| 0.5 | 160 | 380 | 131 | 473 | 146 | 437 | | | 180 | 383 |
| P 1075 | | | | | $LD_{50}$ 1000 mg/kg p.o. (mice) | | | | | |
| 0.05 | 170 | 340 | 105 | 450 | 102 | 432 | | | 164 | 348 |
| Minoxidil:* | | | | | $LD_{50}$ > 1000 mg/kg p.o. (mice) | | | | | |
| 1.0 | 170 | 371 | 158 | 431 | 146 | 424 | | | 169 | 407 |
| 0.5 | 163 | 380 | 161 | 409 | 153 | 411 | | | 167 | 400 |
| Hydralazine: | | | | | $LD_{50}$ - 122 mg/kg (114–130) (mice) | | | | | |
| 5.0 | 170 | 368 | 150 | 405 | 152 | 410 | | | 170 | 380 |
| 2.0 | 181 | 389 | 162 | 425 | 163 | 413 | | | 174 | 379 |

BP Mean arterial blood pressure in mm Hg
HR Heart rate in beats/minute
UV Urine volume in ml
*Minoxidil 6-Amino-1,2-dihydro-1-hydroxy-2-imino-4-piperid-1-ylpyrimidine

EXAMPLE 42

Hypotensive activity in conscious normotensive dogs

Mongrel dogs of both sexes, fasting 16 hours before the experiment were used. Blood pressure was recorded indirectly with an ultrasonic instrument (Arteriosonde ® 1010, Roche Medical Electronic Division) before the administration of P 1060 or P 1075 and then after 1, 2, 3 and 4 hours. The compounds were orally administered in gelatine capsules. Table 3 reports the results obtained with the two compounds.

TABLE 3

| | Dog | | | | | | | | |
|---|---|---|---|---|---|---|---|---|---|
| | I | | | II | | | III | | |
| hours | BP | HR | UV | BP | HR | UV | BP | HR | UV |
| −2 | 90 | 108 | 5.0 | 110 | 108 | 7.5 | 120 | 80 | 24 |
| −1 | 100 | 100 | 8.5 | 105 | 80 | 8 | 125 | 76 | 20 |
| P 1060 | | | | | | | | | |
| 0.1 mg/kg | | | | | | | | | |
| 1 | 75 | 152 | 2.3 | 100 | 112 | 8 | 65 | 172 | 22 |
| 2 | 80 | 180 | 7.1 | 95 | 128 | 12.5 | 115 | 104 | 20 |
| 3 | 90 | 152 | 11 | 95 | 104 | 22.5 | 110 | 92 | 12 |
| 4 | 120 | 140 | 22 | 105 | 100 | 16 | 125 | 88 | 14 |
| −2 | 95 | 105 | | 105 | 85 | | 120 | 105 | |
| −1 | 105 | 112 | | 115 | 105 | | 125 | 110 | |
| P 1075 | | | | | | | | | |
| 0.1 mg/kg | | | | | | | | | |
| 1 | 72 | 160 | | 82 | 175 | | 95 | 185 | |
| 2 | 75 | 180 | | 74 | 185 | | 90 | 175 | |
| 3 | 85 | 142 | | 92 | 163 | | 104 | 149 | |
| 4 | 95 | 135 | | 115 | 140 | | 110 | 140 | |

BP Mean arterial blood pressure in mm Hg
HR Heart rate in beats/minute
UV Urine volume in ml

EXAMPLE 43

Hypotensive action and various cardiovascular and autonomic responses in cats.

Cats of both sexes anaestetized with pentobarbital 40 mg i.p. were used. The left carotid artery was exposed and cannulated with polyethylene cannula connected through a Statham pressure transducer to a Grass Polygraph Recorder. The right femoral vein was also cannulated for the administration of P 1060. The compound was administered dissolved in dilute HCl in a volume of 0.4 ml. Measurements were made before and after intravenous administration of P 1060 of the vasopressor response to intravenously administered norepinephrine hydrochloride (1 meg/kg), (NE) or to common carotid artery occulusion(45 secs), (CO). Both procedures are known to produce pressor effects. Moreover the contraction of nictitating membrane induced by preganglionic (3 V, 1 msec. 40 Hz for 5 secs.) and postganglionic (3 V, 1 msec. 40 H for 5 secs.) stimulation was measured before and after intravenous administration of P 1060. Table 4 reports in detail the results obtained.

TABLE 4

| Treat-ment | Dose mg/kg i.v. | ΔBP mm Hg | ΔHR beats/min. | % reduction NE | CO | Nict. pre | Membr. post |
|---|---|---|---|---|---|---|---|
| P 1060 | 0.01 | 90 | 20 | 50 | 100 | | |
| — | 0.01 | 90 | 35 | | | 20 | 12 |
| — | 0.05 | 110 | 30 | | | 12 | 21 |

EXAMPLE 44

N-tert-Butyl-N''-cyano-N'-4-pyridylguanidine

By following the procedure of Example 1, but substituting N-tert-butyl-N'-4-pyridylcarbodiimide for N-tert-butyl-N'-3-pyridylcarbodiimide, the desired compound was obtained with a melting point of 203.0°-204.0° C. IR(KBr) showed a strong absorption band at 2175 $cm^{-1}$(—C≡N).

EXAMPLE 45

N''-Cyano-N-tert-penyl-N'-4- pyridylguanidine

By following the procedure of Example 1, but substituting N-tert-pentyl-N'-4-pyridylcarbodiimide for N-tert-butyl-N'-3-pyridylcarbodiimide, the desired compound was obtained with a melting point of 161.0°-162.0° C.

EXAMPLE 46

N''-Cyano-N-1-ethylpropyl-N'-4-pyridylguanidine

By following the procedure of Example 1, but substituting N-1-ethylpropyl-N'-4-pyridylcarbodiimide for N-tert-butyl-N'-3-pyridylcarbodiimide, the desired compound was obtained with a melting point of 196.0°-197.0° C.

EXAMPLE 47

N''-Cyano-N-4-pyridyl-N'-1,2,2-trimethylpropylguanidine

By following the procedure of Example 1, but substituting N-4-pyridyl-N'-1,2,2-trimethylpropylcarbodiimide for N-tert-butyl-N'-3-pyridylcarbodiimide, the desired compound was obtained with a melting point of 164.0°-165.0° C.+)

+)monohydrate

EXAMPLE 48

N''-Cyano-N-4-pyridyl-N'-1,1,3-trimethylbutylguanidine

By following the procedure of Example 1, but substituting N-4-pyridyl-N'-1,1,3-trimethylbutylcarbodiimide for N-tert-butyl-N'-3-pyridylcarbodiimide, the desired compound was obtained with a melting point of 155.0°-156.0° C.

EXAMPLE 49

N''-Cyano-N-1,1-diethylpropyl-N'-4-pyridylguanidine

By following the procedure of Example 1, but substituting N-1,1-diethylpropyl-N'-4-pyridylcarbodiimide for N-tert-butyl-N'-3-pyridylcarbodiimide, the desired compound was obtained with a melting point of 220.0°-221.0° C.

EXAMPLE 50

N''-Cyano-N-4-pyridyl-N'-1,1,3,3-tetramethylbutylguanidine

By following the procedure of Example 1, but substituting N-4-pyridyl-N'-1,1,3,3-tetramethylbutylcarbodiimide for N-tert-butyl-N'-3-pyridylcarbodiimide, the desired compound was obtained with a melting point of 197.0°-198.0° C.

EXAMPLE 51

N''-Cyano-N-1,5-dimethylhexyl-N'-4-pyridylguanidine

By following the procedure of Example 1, but substituting N-1,5-dimethylhexyl-N'-4-pyridylcarbodiimide for N-tert-butyl-N'-3-pyridylcarbodiimide, the desired compound was obtained with a melting point of 136.0°-137.0° C.

EXAMPLE 52

N''-Cyano-N-cyclooctyl-N'-4-pyridylguanidine

By following the procedure of Example 1, but substituting N-cyclooctyl-N'-4- pyridylcarbodiimide for N-tert-butyl-N'-3-pyridylcarbodiimide, the desired compound was obtained with a melting point of 198.0°-199.0° C.

EXAMPLE 53

N''-Cyano-N-neopentyl-N'-4-pyridylguanidine

By following the procedure of Example 1, but substituting N-neopentyl-N'-4-pyridylcarbodiimide for N-tert-butyl-N'-3-pyridylcarbodiimide, the desired compound was obtained.

EXAMPLE 54

N''-Cyano-N-4-pyridyl-N'-1,1,2-trimethylpropylguanidine

By following the procedure of Example 1, but substituting N-4-pyridyl-N'-1,1,2-trimethylpropylcarbodiimide for N-tert-butyl-N'-3-pyridylcarbodiimide, the desired compound was obtained. The IR spectrum (KBr) had a strong absorption band at 2160-70 $cm^{-1}$.

EXAMPLE 55

N-Benzyl-N''-cyano-N'-4-pyridylguanidine

By following the procedure of Example 1, but substituting N-benzyl-N'-4-pyridylcarbodiimide for N-tert-butyl-N'-3-pyridylcarbodiimide, the desired compound was obtained.

EXAMPLE 56

N-tert-Butyl-N''-cyano-N'-3-(2,4,6-trimethylpyridyl)-guanidine

3-Amino-2,4,6-trimethylpyridine (1.36 g) and S-methyl-N-tert-butyl-N'-cyanoisothiourea (1.71 g) were refluxed in pyridine (10 ml) for 48 hours. Pyridine was removed in vacuo, and the residue was recrystallized from aqueous ethanol to yield the desired compound. Melting point: 187.0°-188.0° C.

EXAMPLE 57

N''-Cyano-N-tert-pentyl-N'-3-(2,4,6-trimethylpyridyl)-guanidine

By following the procedure of Example 56, but substituting S-methyl-N-tert-pentyl-N'-cyanoisothiourea for S-methyl-N-tert-butyl-N'-cyanoisothiourea, the title compound was obtained with a melting point of 163.0°-164.0° C.

EXAMPLE 58

N-tert-Butyl-N''-cyano-N'-3-quinolylguanidine

By following the procedure of Example 1, but substituting N-tert-butyl-N'-3-quinolylcarbodiimide for N-tert-butyl-N'-3-pyridylcarbodiimide, the desired compound was obtained with a melting point of 228.5°-229.0° C.

EXAMPLE 59

N-tert-Butyl-N''-cyano-N'-3-pyridylguanidine

N-tert-butyl-N'-3-pyridylthiourea (2.1 g) and lead cyanamide (3.7 g) were refluxed in ethanol (20 ml) for 18 hours. The mixture was filtered, and the filtrate was evaporated in vacuo to afford the crude product. Recrystallization from aqueous acetone gave the desired compound. Melting point 205.0°-206.5° C.

What we claim is:

1. A compound of the formula I

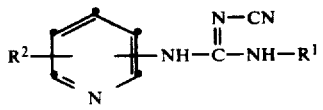

or the tautomeric forms thereof in which the $R^1$-substituted cyano-guanidyl radical is placed in the 2-, 3- or 4-position of the pyridine ring, and in which $R^1$ stands for aliphatic hydrocarbon having from 1 to 8 carbon atoms, cycloalkyl having from 3 to 8 carbon atoms, phenyl, benzyl or phenethyl, and $R^2$ stands for hydrogen, halogen, hydroxy, lower alkyl or lower alkoxy radicals, or a salt thereof with a non-toxic, pharmaceutically acceptable acid.

2. A compound according to claim 1 in which the $R^1$-substituted cyano-guanidyl radical is placed in the 3-position of the pyridine ring.

3. A compound according to claim 1, in which the $R^1$-substituted cyano-guanidyl radical is placed in the 4-position of the pyridine ring.

4. A compound according to claim 1, in which $R^1$ is selected from the group consisting of isopropyl, isobutyl, sec-butyl, tert-butyl, branched pentyl, branched hexyl and branched heptyl.

5. A compound as defined in claim 1 which is N-tert-butyl-N''-cyano-N'-3-pyridylguanidine; or a non-toxic, pharmaceutically-acceptable acid-addition salt thereof.

6. A compound as defined in claim 1 which is N''-cyano-N-tert-pentyl-N'-3-pyridylguanidine; or a non-toxic, pharmaceutically-acceptable acid-addition salt thereof.

7. A compound as defined in claim 1 which is N''-cyano-N-(1-ethyl-1-methylpropyl)-N'-3-pyridylguanidine; or a non-toxic, pharmaceutically-acceptable acid-addition salt thereof.

8. A compound as defined in claim 1 which is N''-cyano-N-3-pyridyl-N'-1,1,2-trimethylpropylguanidine; or a non-toxic, pharmaceutically-acceptable acid-addition salt thereof.

9. A compound as defined in claim 1 which is N''-cyano-N-(1,1-diethylpropyl)-N'-3-pyridylguanidine; or a non-toxic, pharmaceutically-acceptable acid-addition salt thereof.

10. A compound as defined in claim 1 which is N''-cyano-N-neopentyl-N'-3-pyridylguanidine; or a non-toxic, pharmaceutically-acceptable acid-addition salt thereof.

11. A compound according to claim 1 wherein $R^1$ is either saturated hydrocarbon or

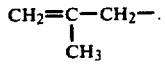

12. A composition for the treatment of hypertension containing as an active component, an effective amount of at least one compound according to claim 1, together with a carrier therefor.

13. A composition according to claim 12, which contains at least 0.1% of the active compound.

14. A composition according to claim 12 containing at least 0.1% of said compound in combination with another therapeutic compound applied in the treatment of hypertension, together with a pharmaceutical carrier.

15. A composition according to claim 14, which also contains an effective amount of a $\beta$-adrenergic blocker, a diuretic, reserpine, or $\alpha$-methyldopa.

16. A composition according to claim 14, which contains an effective amount of a $\beta$-adrenergic blocker.

17. A method of treating a human suffering from hypertension which comprises administering an effective amount of a compound of the formula I

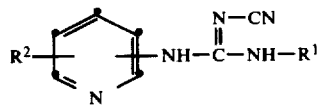

or the tautomeric forms thereof in which the $R^1$-substituted cyano-guanidyl radical is placed in the 2-, 3- or 4-position of the pyridine ring, and in which $R^1$ stands for aliphatic hydrocarbon having from 1 to 8 carbon atoms, cycloalkyl having from 3 to 8 carbon atoms, phenyl, benzyl or phenethyl, and $R^2$ stands for hydrogen, halogen, hydroxy, lower alkyl or lower alkoxy radicals; or a salt thereof with a non-toxic, pharmaceutically acceptable acid.

18. A method as claimed in claim 17, in which the compound is administered to an adult in dosage units containing not less than 0.01 mg and up to 1000 mg.

19. A method as claimed in claim 18 wherein the compound is administered in a dosage unit of from 0.02 to 200 mg.

*20. A compound as defined in claim 1 which is N''-cyano-N-4-pyridyl-N'-1,2,2-trimethylpropylguanidine; or a non-toxic, pharmaceutically acceptable acid addition salt thereof.*

*21. A composition for the treatment of hypertension containing as an active component, an effective amount of a compound according to claim 20, together with a carrier therefor.*

*22. A method as claimed in claim 17 in which the compound is N''-cyano-N-4-pyridyl-N'-1,2,2-trimethylpropylguanidine.*

* * * * *